United States Patent [19]

Riley et al.

[11] 4,133,928

[45] Jan. 9, 1979

[54] FIBER REINFORCING COMPOSITES COMPRISING PORTLAND CEMENT HAVING EMBEDDED THEREIN PRECOMBINED ABSORBENT AND REINFORCING FIBERS

[75] Inventors: Victor Riley; Ian Macnab; John Timusk, all of Toronto, Canada; Edward English, Downey, Calif.

[73] Assignee: The Governing Council of the University of Toronto, Toronto, Canada

[21] Appl. No.: 828,921

[22] Filed: Aug. 29, 1977

Related U.S. Application Data

[60] Continuation of Ser. No. 586,140, Jun. 11, 1975, Pat. No. 4,076,884, which is a division of Ser. No. 343,863, Mar. 22, 1973, Pat. No. 3,903,879.

[30] Foreign Application Priority Data

Mar. 22, 1972 [GB] United Kingdom ............... 13333/72

[51] Int. Cl.² ................................................ B32B 7/00

[52] U.S. Cl. ................................. 428/255; 52/309.17; 52/659; 428/257; 428/259; 428/280; 428/310; 428/446; 428/539; 264/228

[58] Field of Search ............ 128/91 R; 428/255, 258, 428/259, 280, 245, 247, 289, 310 HC, 446, 539; 52/309.17, 659

[56] References Cited

U.S. PATENT DOCUMENTS

| 2,372,983 | 4/1945 | Richardson | 128/91 R |
| 3,332,416 | 7/1967 | Brickman et al. | 128/91 R |

FOREIGN PATENT DOCUMENTS

742497  9/1966  Canada .................................. 128/91 R

*Primary Examiner*—James J. Bell
*Attorney, Agent, or Firm*—Hirons & Rogers

[57] ABSTRACT

Fibre reinforced composites of cementitious materials or gypsum are reinforced with pre-combined mixtures of strong reinforcing fibres e.g., glass or steel, and water absorbent fibres, e.g., cotton. Examples of composites are cement pipes, wall boards, etc.

7 Claims, No Drawings

FIBER REINFORCING COMPOSITES COMPRISING PORTLAND CEMENT HAVING EMBEDDED THEREIN PRECOMBINED ABSORBENT AND REINFORCING FIBERS

This is a continuation of U.S. patent application Ser. No. 586,140 filed June 11, 1975, and issued Feb. 28, 1978 as U.S. Pat. No. 4,076,884, which application was itself a division of U.S. patent application Ser. No. 343,863 filed March 22, 1973, and now issued September 9, 1975 as U.S. Pat. No. 3,903,879.

FIELD OF THE INVENTION

This invention relates to fibre reinforced composites of the type in which gypsum or inorganic cementitious matrix materials are reinforced by fibres, and to methods for their preparation.

BRIEF DESCRIPTION OF THE PRIOR ART

Fibre reinforced composites of cementitious materials with various strength — conferring fibres are known. Examples are asbestos-cement sheets, and steel fibre — and steel wire — reinforced composites known as ferrocement structures.

Several methods are known for preparing such cementitious composites. A first method is simple mixing of short reinforcing fibres (asbestos or chopped glass, for example), with the matrix material in fluid form (e.g. a slurry of portland cement paste), and subsequent hardening. In such a method, the fibres are generally damaged during mixing. The strength of the composite is low, because the fibres are randomly oriented. The amount of chopped fibres which can be added is limited, since the fibres greatly increase the viscosity of the matrix material, when it is in its liquid form. As this viscosity increases, it becomes increasingly difficult properly to coat the fibres. With cementitious slurries e.g. portland cement paste, increasing the dilution of the slurry reduces the viscosity, but at the same time reduces the strength of the hardened material. One can concentrate the slurry after coating and before hardening, e.g. by drawing excess moisture under vacuum, but this adds an expensive process step.

In a second method, reinforcing fibres, filaments, wires or rods are shaped, laid up or woven over on or in a mold armature or form and impregnated with fluid matrix materials, for example in the production of ferrocement boat hulls or steel reinforced concrete structures. Such a process is time-consuming and expensive, involving manual operations.

SUMMARY OF THE INVENTION

It is an object of the present invention to provide novel composites of cementitious or gypsum matrix materials and fibres.

A further object is to provide new methods of making composites of cementitious or gypsum matrix materials and fibres, which are versatile and economical.

A further object is to provide novel fibre combinations useful in reinforcing such composites.

Other objects will be apparent from the following description and specification.

Briefly, these objects are accomplished in accordance with the invention by the provision of fibre reinforced composites of cementitious matrix materials and gypsum matrix materials of improved strength and other properties, having precombined absorbent fibres and reinforcing fibres, as the reinforcement.

By "cementitious matrix materials" as used herein is meant inorganic cement based hardenable materials. The term does not include gypsum based materials, to which different considerations apply, and which are separately identified herein.

The absorbent carrier fibres used in the present invention are generally textile fibres, for example natural fibres such as cotton, wool, hemp, abaca, silk, sisal, jute, flax and cellulose (paper or wood), regenerated fibres such as viscose rayon, cuprammonium rayon and cellulose acetate or absorbent synthetic fibres such as nylon 66, polyacrylonitrile, or polyvinyl alcohol and absorbent types of polyesters or polyacrylics. Preferred among such fibres are cotton, wool, cellulose, viscose rayon and cuprammonium rayon, with the most preferred being cotton and rayon, generally on account of cheapness and desirable absorbence. The terms absorbent and non-absorbent used herein refer to the behaviour of fibres towards aqueous cementitious slurries. Absorbent fibres have a moisture regain under standard conditions (65% relative humidity at 20° C.) above about $2\frac{1}{2}\%$.

The reinforcing fibres used in the present invention are non absorbent and are those commonly used in preparing cementitious composites, and include fibres of glass, steel, carbon, boron, copper, brass, aluminum and its alloys, asbestos and silicon compounds, as well as non-absorbent, strong types of synthetic polymeric fibres such as non-absorbent polyamides, non-absorbent polyesters, non-absorbent polyacrylics, polyolefins such as polyethylene and polyurethanes. Preferred are fibres of glass, steel, carbon, polyethylene and polypropylene. The reinforcing action is believed derived largely from the reinforcing fibres alone. However, the presence of the absorbent carrier fibres appears to facilitate coating or impregnating the mixture of fibres with the matrix material, by providing the necessary adhesion therebetween.

DESCRIPTION OF THE PREFERRED EMBODIMENTS

It is preferred to unite the absorbent fibres and reinforcing fibres prior to application of the matrix material, to make a fibre combination. This combination can be a single reinforcing fibre twisted with an absorbent fibre, or a multi-ply yarn of several absorbent and reinforcing fibres spun together. The reinforcing fibres and carrier fibres can be inter-woven together, into a mesh, cloth or tape. The aforementioned multi-ply yarn or twisted fibre combination can be woven into a cloth, mesh or tape. Meshes etc., with fibres spaces at intervals of about 4 to about 30 ends per inch are preferred. These fibre combinations can be easily coated or impregnated with matrix materials such as slurries of portland cement paste or gypsum, even though these materials generally do not adhere to reinforcing fibres alone. The term "reinforcing fibres" is intended to include the materials in the forms of whiskers, flakes, ribbons, filaments, strands, lovings, etc.

It has been found that, in addition to assisting in pickup of cement or gypsum pastes, the absorbent fibres in the composites of this invention increase the interlaminar bond strength significantly. Thus they increase the bond strength between successive layers of impregnated fibres.

Once the fibre combinations impregnated with matrix material have been prepared, they can be used in a variety of ways to provide high quality composite materials in an efficient manner. They can be chopped into small lengths before or after impregnation with the matrix material and molded in accordance with the first process described, although there is little advantage in such a process, under most circumstances. They can be molded into composite shapes in the form of cloths or meshes, in accordance with the second process described, where the matrix material is impregnated before or after molding. Preferably, however, they are used for molding composites by winding or arranging the impregnated combination into the desired shapes and hardening.

An application of this invention is in steel wire reinforced concrete. In normal process, such structures are made by mixing about 2% by weight of chopped steel fibres, about 10 mils diameter and 1" in length, in ordinary portland cement concrete. There is a tendency for fibres in this process to become damaged during mixing. In accordance with the present invention, one can make combination tapes of high strength steel wires and cotton yarn, by weaving on a shuttle type loom. Use of such tapes in steel wire reinforced concrete gives superior properties. As previously disclosed, one can substitute other strong fibres, such as glass, etc., for the steel.

Having prepared preformed tapes of interwoven strong fibres and reinforcing fibres, one can then impregnate these with aqueous cementitious slurries. Then the impregnated tapes can be laid up in the desired manner to fabricate finished articles by drying and hardening the cementitious matrix materials.

For example, the impregnated tapes may be wound spirally over a cylindrical mandrel, to form fibre reinforced cement pipes. Layers of the impregnated tapes may be built up within shaped, removable forms or moulds, to make articles such as fibre-cement boat hulls, or fibre-cement building blocks, wallboards, tanks, etc. Methods of fabricating articles somewhat resemble known techniques for making glass fibre resin reinforced items, where glass fibre tapes are impregnated with resins, put into molds and hardened, or laid side by side on preformed structures and hardened in situ or wound onto preformed structures and hardened in situ. The presence of the absorbent fibres in the composites of this invention ensures pickup of sufficient cementitious slurry to form satisfactory finished articles.

Instead of impregnating the pre-woven tapes, one can lay up the tapes in the mold or where else they are to be fabricated, and then pour cement slurry over them. A further alternative is to apply a mixture of cementitious matrix materials and volatile solvents, e.g. ethyl alcohol to the webs, and after evaporation of the volatile solvents lay them in the mold or elsewhere and apply water to them. Cement slurry can be applied by brush or rolling onto the tapes, instead of by dipping.

As noted, it is preferred to use combinations of fibres which have previously been mechanically combined such as interwoven into tapes or sheets. It is also preferred to use either steel or thermoplastic organic polymer coated glass fibres as the reinforcing fibres. Uncoated glass is subject to attack by alkalis present in the cement. If desired, coated or galvanized steel fibres can also be used, so as to avoid any corrosion of such fibres at the surfaces of finished articles.

A preferred reinforcing fibre in glass fibre yarn coated with a thermoplastic polymer, prior to forming the fibre combination.

This thermoplastic coating performs several functions. It enhances the adhesion between the cement on gypsum and glass fibres, to increase the flexural strength of the composite. It has been found that the shear bond strength between polyethylene coated glass fibre and gypsum is about 6 times that between uncoated glass fibre and gypsum. It protects the glass fibre from physical damage during handling, weaving, cutting, packaging etc., and from damage by water solvents or chemical attack. Uncoated glass yarn is so sensitive that it can easily lose 50% of its strength by damage during slight handling. The coating also assists in stabilising the form of the web, by increasing the surface friction of the glass fibres and by producing "weldable" points of intersection of fibres. The use of uncoated glass fibres and cotton, etc., would not produce stable webs with ordinary gauze stitch, because the lack of friction between fibres would cause displacement of fibres. One way of avoiding this is to employ a leno stitch at the fibre intersections, but this cannot be used with glass fibres because normal glass fibres lack the necessary degree of flexibility to allow leno stitching without breaking. With the coated glass fibres in the present invention, simple gauze stitching is satisfactory. In addition, bonds can be formed at the fibre intersections by heat softening, e.g. by passing the web through heated press rollers. This keeps the web intact and prevents pull-out of individual fibres. The surface friction can be controlled by changing the roughness of the coating on application.

Examples of suitable coatings are polyethylene, polyvinyl chloride, polypropylene, nylon, polystyrene, silicones and other inert polymeric materials. Polyvinyl Chloride, polyethylene, polypropylene and nylon are preferred.

Methods of preparing such resin coated glass fibres include extrusion methods and fluidized bed coatings. In extrusion methods, the fibres to be coated are pulled through the coating polymer which is in fluid form, and then through a die opening. The polymer may be heat softened, or in solution in a solvent, or in a dispersion in water. In this method, however, there is a practical minimum of thickness of resin coating which can be achieved. In the fluidized bed method, the cold fibre is passed through a fluidized bed of powdered polymer, and then through a heater to melt the polymer onto the fibre. This allows very thin coatings to be applied. The roughness of the coating can be controlled by pre-soaking the fibre in a liquid such as aqueous detergent solution.

The thickness of the coating applied is largely dictated by practical considerations. It should be sufficient to ensure continuous coating over the major proportion of the entire surfaces of the fibres and so that heat softening and pressing will not cause significant voids in the coating to form. On the other hand, too thick a coating makes an impractically bulky fibre and increases the costs without achieving technical benefits. Coatings of thickness about 0.3 to 5 mils are normally satisfactory.

Cementitious or gypsum materials can be further strengthened by adding polymer latices to the paste, or by subsequently impregnating the hardened material with a monomer. Suitable latices include those of vinyl acetate polymers and copolymers, styrene polymers and copolymers, vinyl chloride polymers and copolymers, and polyacrylates. Elastomer latices, e.g. those of butadiene polymers, may also be used. They are suitably used in amounts of 0.15 to 0.25 parts polymer per part by weight of cement or gypsum. For impregnating, methyl methacrylate is a suitable monomer. The hard dry composite may be soaked in the monomer, or vacuum impregnated therewith, and then heated or irradiated to cause polymerization.

The additional strength conferred by the fibre combinations according to the invention means that thinner, lighter cementitious structures can be prepared than previously, without loss of strength. Ferrocement boats, for example, can be made economically in this manner.

Instead of interweaving the fibres to make a web or tape, they can be formed into a felt. This is done using, for example, mixtures of chopped glass fibres and cotton, paper or wool. These are mixed with a suitable adhesive, e.g. polyvinyl alcohol solution and laid as a felt. Such felts can then be impregnated with cementitious matrix material in fluid form, and allowed to harden. Whilst such composites are not as strong as those based on pre-woven tapes, they are cheaper, and allow use of very cheap fibrous materials e.g. paper fibres.

The composites of the invention can also be used to effect repairs to concrete structures, e.g. swimming pools. Combination tapes of the invention can be impregnated with cementitious matrix materials preferably latex modified cement, and smoothed on the concrete surface, in one or more layers.

The following are illustrative specific examples.

EXAMPLE 1

Steel wire reinforced concrete was prepared in accordance with the present invention, as follows.

Four inch wide tapes of high strength steel wires and cotton yarn were woven on a shuttle type loom, to give a fibre combination. The steel wire had a diameter of 6 mils and a strength of about 400,000 p.s.i. The cotton used was preshrunk two ply No. 30 bleached yarn. Ten ends per inch for each fibre was used in both the longitudinal (warp) and cross (weft) directions.

The tapes, after this preparation, were passed through a portland cement mortar slurry consisting of one part water, two parts cement, three parts sand by weight, and then were wound into a cylindrical mold. The mold was then placed in a standard moisture curing room for one month. The cylindrical shell of reinforced concrete was then removed from the mold, and was found to exhibit about three times the flexural strength, and about twenty to thirty times the facture toughness which could be obtained from mortar reinforced with equal weight fractions of chopped steel wires.

Similar shell type structure could be produced by winding the wire into the same mold, and then trowelling in the mortar, in accordance with previously known processes. However, the trowelling operation is extremely time-consuming, is likely to damage the fibres, and leads to an uneven wall thickness in the structure. In accordance with the present invention, a combination steel wire/cotton yarn tape is used which is impregnated before application of the mortar. This provides high quality structure at low fabrication cost, and the steel wires can be aligned in any direction desired. In addition, the wall thickness of the structure can be controlled within close tolerances.

The fabrication technique can be used in the production of shell structures such as grain bins, or crude oil tanks. It can also be used to provide modular housing units.

EXAMPLE 2

Gypsum board was made using fibre combinations of the invention.

A glass/cotton tape was prepared, using a PVC coated glass yarn, pre-twisted with 2 ply No. 50 bleached cotton, woven into a 6 inch wide tape with 12 ends per inch composite yarn in the longitudinal (warp) direction and 22 ends per inch in the transverse (weft) direction. The gypsum was plaster of paris β-hemihydrate, and contained 1% Keratin to retard setting up of the gypsum. A slurry was made using 0.55 parts water per part gypsum.

Pieces of tape 6 inches by 12 inches were cut, dipped in the slurry and placed on a release coated surface, in a pile. The pile was pressed to remove air bubbles. This produced a 4-layer gypsum/fibre board of thickness about ⅜ inch, which was allowed to harden for 1 week. A control was also prepared, of the same thickness, using no fibres. The samples were then tested for strength with specimens cut out in the lengthwise direction. Modulus of rupture and fracture toughness were determined using an Instron Universal Tester, by three point bending. Lateral nail resistance was tested by driving in a 0.116 inch diameter nail, ½ inch from the sample edge and pulling it out with the Instron tester. The results were as follows:

|  | Modulus of rupture (p.s.i.) | Fracture toughness (in.lb.) | Lateral nail Resistance |
|---|---|---|---|
| Reinforced gypsum board | 1360 | 36.0 | 120.0 |
| Control gypsum board | 850 | 1.9 | 14.0 |

The fibre reinforced boards can be used in place of plywood in many applications. The process of this invention gives strong, tough, high quality wall or floor boards efficiently and economically. They can be strengthened even further by incorporation in the gypsum of a polymer latex, such as a polyvinyl or polyvinylidene chloride latex.

EXAMPLE 3

Glass reinforced high alumina cement composites were prepared, using 12 inch wide tapes of composited yarn of pretwisted glass yarn and 2-ply No. 30 bleached cotton. The tape was woven in a standard shuttle type textile loom, to give 22 ends per inch in both directions.

Pieces of tape 6 by 12" were impregnated with high alumina cement slurry, containing 0.55 parts water per part cement. The sheets were piled 16 high on a release coated surface to give a composite of thickness 3/16". A control sample of the same thickness without fibrous layer reinforcement, was prepared of the same cement. Both were left to dry and harden for one week, then tested as in Example 3, with the following results.

|  | Modulus of Rupture (psi) | Fracture Toughness (in lbs.) |
|---|---|---|
| Fibre reinforced composite | 3960 | 62.1 |
| Control | 550 | 2.3 |

High alumina cement is desirable for use with uncoated glass fibres, since it does not release alkali. With regular cement, coated glass is preferred, for resisting alkali.

EXAMPLE 4

Steel wire reinforced mortar was prepared according to the invention.

Alternate layers of fine steel wire mesh and leno stitched cotton gauze were impregnated with latex modified portland cement paste. The latex was a styrene-butadiene latex, used in an amount of 0–15 parts latex solids per part cement. 8 layers of steel wire and 9 pieces impregnated cotton were piled alternately to make a board about ⅜" thick. Whilst the steel wire mesh was run through the cement paste also, it picked up virtually no cement. Controls of unreinforced cement and unreinforced latex impregnated cement were made to the same thickness, and all specimens hardened for one week. Flexural strength tests were conducted as in Example 3, with the following results:

|  | Modulus of Rupture(psi) | Fracture Toughness (lb.in) | Strain to First Crack(%) |
|---|---|---|---|
| Reinforced latex modified cement | 3180 | 38.2 | 0.12 |
| Latex modified cement control | 640 | 3.5 | 0.10 |
| cement control | 520 | 2.0 | 0.03 |

A further specific embodiment of the invention is a medical cast. Conventionally, casts are made by impregnating a cotton bandage with gypsum slurry and wrapping the bandage around a fracture site. Since cotton fibres provide weak reinforcement, the cast has to be bulky and heavy, to have the necessary strength. Whilst proposals have been made to use stronger fibres, such as glass fibres, these have not found wide acceptance. One of the problems is lack of adhesion of gypsum slurries to fibres such as glass.

The casts according to the present invention use bandages of combined reinforcing fibres, preferably glass, and absorbent fibres, preferably cotton. The glass fibres are coated with a thermoplastic vinyl resin, in accordance with the previous description, prior to forming the combination bandage. In addition to providing advantages previously discussed, when used in casts the coating prevents irritation of surgeon's or patient's skin. For use in casts, polyethylene and polyvinyl chloride coatings are preferred.

Bandages for casts according to this invention preferably are interwoven of absorbent (e.g. cotton) fibres in the longitudinal direction and coated glass fibres in the transverse direction. For proper application, is is preferred that the bandage be stretchable longitudinally, which is not achieved with coated glass fibres, unless special, very fine glass fibres are used. Conversely, inextensibility as provided by glass fibres is desirable in the transverse direction for fracture immobilization. Mixtures of cotton and glass fibres can alternatively be used in the transverse direction, the fibres being either precombined e.g. by intertwining, or separately woven into the bandage. The preferred interwoven bandages have the additional but subjective advantage of acceptable feel and handle to the surgeon, similar to well established cotton bandages.

The following illustrates a cast according to the invention

EXAMPLE 5

A glass reinforced plaster cast, for immobilizing a fracture, was prepared as follows. A bandage, 12" in width, was prepared out of cotton and glass yarn 8 mil thick. This combination bandage was woven on a shuttle type loom. Prior to weaving the glass yarn was coated with a vinyl plastic, specifically polyvinyl chloride, by an extrusion process. After coating, the glass fibres had a diameter of 11 mils and a strength of about 200,000psi. The cotton used was pre-shrunk two ply No. 30 bleached yarn. In the longitudinal or warp direction of the bandage, cotton only was used, with 22 ends per inch. In the cross or weft direction, the coated glass fibre yarn was used alone, with 16 ends per inch.

The composite bandage thus made was impregnated with a gypsum slurry easily, and slit to a width of about 4". It could be applied to a fracture site as easily as a conventional cotton bandage. Laboratory testing showed that the glass reinforced plaster cast according to the invention had approximately five times the flexural strength, twice the elastic modulus and 1½ times the fracture toughness of conventional plaster casts in the direction of the glass reinforcement. Further, medical trials showed that the glass reinforced cast did not cause irritation of the patient, was much more durable, and could be removed by conventional means.

In application, the surgeon can wind the bandage in both clockwise and counterclockwise directions around the fractured limb, to provide glass fibres which are aligned in two directions slightly offset from the longitudinal direction of the cast.

What we claim as our invention is:

1. Fibre reinforced composite comprising a portland cementitious matrix material having embedded therein precombined absorbent fibres and reinforcing fibres, said absorbent fibres being selected from the group consisting of cotton, wool, cellulose, viscose rayon and cuprammonium rayon, and the reinforcing fibres being selected from the group consisting of glass, steel, carbon, polyethylene and polypropylene.

2. Composite of claim 1 wherein the fibres are precombined together by a process selected from the group consisting of twisting together said selected reinforcing fibre and said selected absorbent fibre, spinning together said selected absorbent fibre and said selected reinforcing fibre into a multiply yarn, interweaving said selected absorbent fibre and said selected reinforcing fibre into a mesh, interweaving twisted together said selected absorbent fibre and said selected reinforcing fibre into a mesh, and interweaving said multiply yarn prepared as aforesaid into a mesh.

3. Composite of claim 1 wherein the reinforcing fibre is glass or steel, the absorbent fibre is cotton or rayon, and the reinforcing fibre and the absorbent fibre are present in an interwoven mesh.

4. Composite of claim 3 wherein the interwoven mesh has fibres spaced at intervals of about 4 to about 30 ends per inch.

5. Composite of claim 1 wherein the fibres are precombined together as a felt.

6. Composite according to claim 1 wherein the reinforcing fibre is thermoplastic organic polymer coated glass yarn, and the reinforcing fibre and the absorbent fibre are present in an interwoven mesh.

7. Composite according to claim 6 wherein the thermoplastic organic polymer coating is polyethylene or polyvinylchloride.